United States Patent [19]

McEntire et al.

[11] Patent Number: 4,675,441
[45] Date of Patent: Jun. 23, 1987

[54] PREPARATION OF N-SUBSTITUTED ACRYLAMIDES

[75] Inventors: Edward E. McEntire; Kathy B. Sellstrom, both of Austin, Tex.

[73] Assignee: Texaco Inc., White Plains, N.Y.

[21] Appl. No.: 836,938

[22] Filed: Mar. 6, 1986

Related U.S. Application Data

[62] Division of Ser. No. 535,017, Sep. 23, 1983, Pat. No. 4,613,673.

[51] Int. Cl.$^4$ ........................................... C07C 102/06
[52] U.S. Cl. ................................. 564/135; 544/168; 546/247; 548/568
[58] Field of Search ....................... 564/135; 544/168; 548/568; 546/247

[56] References Cited

U.S. PATENT DOCUMENTS

| | | | |
|---|---|---|---|
| 2,356,476 | 8/1944 | Shappirio | 44/60 |
| 2,451,436 | 10/1948 | Erickson | 260/561 |
| 2,529,838 | 11/1950 | Erickson | 260/561 |
| 2,649,438 | 8/1953 | Bruson | 260/85.5 |
| 2,719,175 | 9/1955 | Couver et al. | 260/561 |
| 2,867,566 | 1/1959 | Weinberg | 167/53.1 |
| 2,893,857 | 7/1959 | De Pree | 71/2.7 |
| 3,461,147 | 8/1969 | Noltes | 260/429.9 |
| 3,470,220 | 9/1969 | Moedritzer et al. | 260/429 |
| 3,652,671 | 3/1972 | Barron | 260/561 |
| 3,878,247 | 4/1975 | Moss et al. | 260/561 |
| 4,022,831 | 5/1977 | Spoerke | 564/135 |
| 4,031,138 | 6/1977 | Nieh et al. | 564/135 X |
| 4,206,143 | 6/1980 | Wenzel et al. | 260/561 |
| 4,228,102 | 10/1980 | Besecke et al. | 260/561 |
| 4,256,665 | 3/1981 | McEntire | 564/135 |
| 4,256,666 | 3/1981 | McEntire | 564/135 |
| 4,259,259 | 3/1981 | McEntire | 564/137 |
| 4,287,363 | 9/1981 | McEntire | 564/205 |
| 4,309,358 | 1/1982 | Holyoke | 260/429.7 |
| 4,321,411 | 3/1982 | Nakamura et al. | 564/135 |
| 4,358,612 | 11/1982 | Gless | 564/135 X |
| 4,492,801 | 1/1985 | McEntire et al. | 564/135 |

FOREIGN PATENT DOCUMENTS 3048020 12/1980 Fed. Rep. of Germany .

OTHER PUBLICATIONS

Chemical Abstracts 66 2641g (1967).
Chemical Abstracts 66 46631x (1967).
Chemical Abstracts 72 101195g (1979).
Chemical Abstracts 79 32337n (1973).
Chemical Abstracts 90 72289g (1979).
Chemical Abstracts 95 204660m (1981).
Chemical Abstracts 96 85083g (1982).
Chemical Abstracts 102 45495x (1985).
Erickson, "The Preparation and Stabilities of Some B-Dialkylaminopropionamides", Jr. Chem. Soc. 74, 6281-6282 (1952).
Sawyer, Organotin Compounds, Marcil Dekker Inc., NY pp. 507-521; 541-547; 553-555 (1971).

Primary Examiner—Paul F. Shaver
Attorney, Agent, or Firm—Jack H. Park; Kenneth R. Priem; Carl G. Ries

[57] ABSTRACT

This invention is directed to novel catalysts characterized as compounds of tin or zinc containing a direct metal-nitrogen bond. The novel catalysts are derived from a primary or secondary amine such as an alkyl amine, a heterocyclic amine, an aromatic amine, etc. The amine is reacted with a tin compound such as a tin chloride, a tin bromide, a tin oxide, or a tin alkoxide. Alternatively, the amine may be reacted with a zinc halide, a zinc alkoxide or an organozinc compound.

In another aspect of the present invention, the novel catalysts are used to catalyze the reaction of an acrylate or methacrylate ester with an amine in order to prepare N-substituted acrylamides or methacrylamides in good yield and with high selectivity.

12 Claims, No Drawings

PREPARATION OF N-SUBSTITUTED ACRYLAMIDES

This is a division of application Ser. No. 535,017, filed Sept. 23, 1983, now U.S. Pat. No. 4,613,673.

BACKGROUND OF THE INVENTION

1. Field of the Invention

This invention relates to tin and zinc catalysts containing nitrogen-metal bonds and to the use of the catalysts for the preparation of N-substituted acrylamides or methacrylamides by the catalytic reaction of an acrylate or methacrylate with an amine.

2. Prior Art

It is well known that certain β-aminopropionamide compounds can be made by reacting dialkylamine compounds with an acrylic acid or ester compound, as described in John G. Erickson's article, "The Preparation and Stabilities of Some β-Dialkylaminopropionamides," J. Am. Chem. Soc. 74, 6281-82 (1952). The reference discloses that N-N-dialkyl β-dialkylaminopropionamides decompose, when heated at temperatures of about 125°-215° C., to the corresponding dialkylamines and N,N-dialkylacrylamides and that the ease of such decomposition decreases from the dibutylamine to the dimethylamine derivatives. Extensive polymerization of the substituted acrylamide products when certain of the β-dialkylaminopropionamides are heated is also described.

It is known to react an alkali metal amide of a secondary alkyl amine with stannic chloride to provide the corresponding tin amide, wherein the amide is bonded directed to the tin, e.g.:

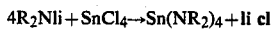

U.S. Pat. No. 2,451,436 to John G. Erickson teaches that N-alkylacrylamides can be prepared by subjecting an N-alkyl β-alkylaminopropionamide, prepared by reacting 2 moles of an alkylamine or dialkylamine with an ester of acrylic or methacrylic acid, to elevated temperatures in the presence of a strong acid catalyst. The patent discloses that the acid catalytic process results in the formation of the salt of the aminoamide which splits when heated into the alkyl amine salt and the N-alkylated acrylamide, the latter distilling off during heating.

U.S. Pat. No. 2,529,838 to John G. Erickson teaches that certain N,N-dialkylacrylamides are produced by heating a dialkylamine containing at least 5 carbon atoms per alkyl group with a monomeric acrylic ester under superatmospheric pressure at temperatures between about 150°-400° C. The reference further teaches that dialkylamines containing fewer than 5 carbon atoms per alkyl group cannot be employed in the disclosed process.

Moreover, these prior art processes have been found to be disadvantageous for the preparation of certain N-(aminoalkyl)acrylamide compounds inasmuch as they typically produce tarry or gummy reaction mixtures from which it is difficult to separate a good yield of pure product. For example, the employment of the acid catalytic process described in U.S. Pat. No. 2,451,436 is reported to result in the production of alkylamino alkyl acrylamides in salt form which are not volatile and, hence, cannot be readily recovered by distillation separation procedures. Moreover, the process described in U.S. Pat. No. 2,529,838 requires very high temperatures and superatmospheric pressures wherein the reactions are of long duration.

In view of these disadvantages, the above-described processes have been considered inapplicable for the preparation of N-(tertiaryaminoalkyl)acrylamides and several alternative processes have been described. For example, U.S. Pat. No. 2,649,438 to Bruson, teaches that certain N-(tertiaryaminoalkyl)acrylamides can be prepared by reacting β-propionlactone,

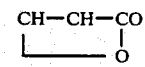

with the desired tertiary amino diamine and distilling the reaction product under reduced pressure whereby dehydration readily occurs. The patent further teaches that other N-(tertiaryaminoalkyl)acrylamides can be obtained by reacting the appropriate acrylyl chloride with the desired tertiary amino diamine.

U.S. Pat. No. 3,652,671 to Barron describes a process for preparing N-(dialkylaminoalkyl)methacrylamides wherein the Michael adduct of methacrylic acid and a N,N-dialkylalkylenediamine; that is, the N-(dialkylaminoalkyl)-2-methyl-β-alanine, is subjected to an elevated temperature of about 140°-230° C. which results in substantially complete rearrangement to the N-(dialkylaminoalkyl)methacrylamide product. This process has the disadvantage of being applicable only to the preparation of N-(dialkylaminoalkyl)methacrylamides which are obtained from methacrylic acid adducts. The patentee teaches that the use of corresponding adducts of acrylic acid in the described process gives poor results with side reactions predominating. The reaction mixtures produced by heating these adducts are stated to be largely by-products and tarry materials from which only small quantities of the desired acrylamide can be separated.

In view of the unavoidable secondary reactions at high temperatures, two-stage processes for the preparation of N-substituted acrylamides or methacrylamides have hitherto proved advantageous. In the process described in U.S. Pat. No. 3,878,247, one mole of an acrylate or methacrylate is reacted with 2 moles of an amine in the first reaction stage at a temperature below 200° C. The Michael addition and aminolysis proceed concomitantly, so that the corresponding β-aminopropionamide or isobutyramide is obtained as an intermediate product. In the second reaction stage the amine added to the double bond is removed at temperatures above 200° C., the substituted acrylamide or methacrylamide being obtained.

In order to avoid undesirable Michael addition, the process described in U.S. Pat. No. 2,719,175 involves the reaction of esters of acrylic or methacrylic acid which amines at 300°-550° C. in the gaseous phase in the presence of solid catalysts such as vanadium-aluminum oxides with contact times of a few seconds to form the corresponding substituted acrylamides or methacrylamides. The high reaction temperature favors uncontrolled decomposition and polymerization reactions, so that yields of at most 50% are obtained.

U.S. Pat. No. 4,206,143 reveals that dialkyl stannic oxide catalysts, such as dibutyl stannic oxide, are effective for the preparation of N-substituted-acrylamides and -methacrylamides from the reaction of an alkyl ester of acrylic or methacrylic acid with an aliphatic, cycloaliphatic or aromatic amine, which is a primary or secondary amine. Similarly, a method whereby methacrylate or acrylate esters are treated with N,N-dialkyldiaminoalkanes in the presence of organotin compounds, such as dibutyldimethoxytin, to give (meth)acrylamides having tertiary amino groups is described in U.S. Pat. No. 4,321,411.

U.S. Pat. NO. 4,228,102 discloses that certain N-substituted acrylamides may be made by reacting an ester with an amine with heating under pressure where the amine is present in an amount which is stoichiometrically deficient up to an amount which is in small stoichiometric excess with respect to the ester. However, the only example therein which is run under those conditions gave the poor yield of 32% to the amide. The other examples of that patent all employ an acidic catalyst to obtain a better yield.

It would be desirable to have a process for the production of N-substituted acrylamides in high yield which could be performed in one step which did not employ corrosive, acidic catalysts or excessive temperature and pressure conditions, which have been problems with the previously described methods.

3. Related Applications

Copending Nieh et al. U.S. patent application Ser. No. 382,858 filed May 28, 1982 now abandoned, and entitled "Production of N-Substituted Acrylamides from Acrylates and Amines over a Dialkyltin Dialkoxide Catalyst" is directed to a one-step process for the preparation of N-substituted acrylamides by reacting an acrylate ester with an amine over a catalytic amount of the dialkyltin dialkoxide catalyst.

Copending U.S. patent application Ser. No. 383,634 filed June 1, 1982 now abandoned, for McEntire et al. and entitled "Production of N-Substituted Acrylamides from Acrylates and Amines over a Group IVB Catalyst" is also directed to a one-step process for the preparation of N-substituted acrylamides by the catalytic reaction of an acrylate ester over an amine with a Group IVB metal catalyst such as a titanium or zirconium tetralkoxide.

Copending McEntire et al. U.S. patent application Ser. No. 469,860 filed Feb. 28, 1983 now U.S. Pat. No. 4,492,801, and entitled "Production of N-Substituted (Meth)Acrylamides from (Meth)Acrylates and Amines over a Metal Alkoxide Catalyst" is also directed to the preparation of N-substituted methacrylamides but by a catalytic process wherein the catalyst is a metal alkoxide catalyst.

SUMMARY OF THE INVENTION

This invention relates to catalysts prepared from certain primary or secondary amines and from stannic oxides, from alkoxides, bromides or chlorides of tin or zinc and from organometallic zinc compounds. The present invention is further directed to a method of making the catalysts.

The invention is also directed to a process for the preparation of N-substituted acrylamides of the formula:

$$\begin{array}{c} R^1 \ O \\ | \ \ || \\ CH_2=C-C-NR^2R^3 \end{array}$$

where $R^1$ is hydrogen or methyl, $R^2$ is hydrogen or lower alkyl of 1 to 4 carbon atoms, and $R^3$ is alkyl, aryl, alkaryl, aralkyl or alkoxyalkyl of one to twenty carbon atoms or

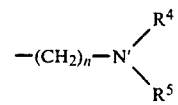

where n is an integer from 2 to 6 and $R^4$ and $R^5$ taken singly are lower alkyl groups of 1 to 4 carbon atoms, or $R^4$ and $R^5$ taken jointly are combined with the N'atom to form a heterocyclic ring group selected from the group consisting of morpholine, pyrrolidine or piperidine ring groups, which process comprises reacting an acrylate ester of the formula $$\begin{array}{c} R^1 \ O \\ | \ \ || \\ CH_2=C-C-O-R^6 \end{array}$$

where $R^1$ is defined as above and $R^6$ is a lower alkyl of 1 to 4 carbon atoms with an amine of the formula $HNR^2R^3$ where $R^2$ and $R^3$ are defined as above over a catalyst having a nitrogen-tin bond or a nitrogen-zinc bond.

DETAILED DESCRIPTION OF THE PREFERRED EMBODIMENTS

The catalysts of the present invention are derived from tin or zinc and are characterized as having a direct nitrogen-metal bond. The catalysts are derived from an amine, a tin compound or a zinc compound.

Known techniques can be used to prepare the catalysts, such as the technique based on reacting a tin halide with an alkali metal amide of a secondary amine. The catalysts can also be prepared in accordance with another aspect of the present invention by reacting a primary or secondary amine with a stannic oxide or with an alkoxide, chloride or bromide of tin or zinc or with an organometallic zinc compound.

The primary or secondary amine may suitably be an alkylamine, a heterocyclic amine or an aromatic amine. The alkyl group may be a straight chain group or a branched chain group or a cyclic alkyl group such as a methyl, ethyl propyl, isopropyl, butyl, isobutyl, tert. butyl, hexyl, cyclohexyl, decyl, etc. containing up to about 20 carbon atoms. The alkyl or aryl group may be further substituted with other unreactive groups such as dialkylamino groups.

Among the heterocyclic amines that may be used are compounds such as morpholine, piperazine, the C-substituted morpholines and piperazines as well as mono N-substituted piperazine such as N-methylpiperazine, N-ethylpiperazine, N-aminoethylpiperazine, etc.

Aromatic amines that may be utilized include analine, substituted anilines, diphenylamine, etc.

The amine of the catalyst may preferably be the amine to be used in the subsequent reaction of the amine with the (meth)acrylate ester. This may eliminate subsequent product separation problems. However, a different amine may be used as illustrated in the examples.

The tin compound to be used in preparing the catalyst compositions in accordance with this aspect of the present invention may suitably be a tin oxide, alkoxide, bromide or chloride, as exemplified by compounds of the formulae:
$R_3SnX$, $R_2SnX_2$, $RSnX_3$, $SnX_4$ or $SnX_2$ Where R is an alkyl group containing from 1 to about 10 carbon atoms and X represents chlorine, bromine, oxygen or a $C_1$ to $C_4$ alkoxide group. Thus, representative compounds that may be used include trimethyltin oxide, triethyltin oxide, tripropyltin oxide, tri-isopropyltin oxide, tributyltin oxide, tri-isopentyltin oxide, trihexyltin oxide, etc.; trimethyltin chloride, triethyltin chloride, tripropyltin chloride, tri-isopropyltin chloride, tributyltin chloride, trihexyltin chloride, and the corresponding bromides; tributyltin methoxide, tributyltin ethoxide, trimethyltin butoxide, etc.; dimethyltin oxide, diethyltin oxide, dipropyltin oxide, dibutyltin oxide, dimethyltin dichloride, diethyltin dichloride, dipropyltin dichloride, dibutyltin dichloride and the corresponding bromides; dimethyltin dimethoxide, dimethyltin diethoxide, diethyltin diethoxide, dibutyltin diethoxide, dibutyltin dipropoxide, dibutyltin dibutoxide, etc.; isopropyltin trimethoxide, isopropyltin triethoxide, butyltin triethoxide, methyltin trichloride, methyltin trichloride, etc; tin tetrachloride, dioctyl tin oxide, etc.

The zinc compound to be used in preparing the catalyst composition of the present invention may suitably be a zinc chloride or bromide, a $C_1$–$C_{18}$ zinc alkoxide or an organo metallic zinc compound such as a dialkyl zinc compound where the alkyl group contains 1 to 4 carbon atoms, such as zinc chloride, zinc bromide, zinc dimethoxide, dimethyl zinc, diethyl zinc, dipropyl zinc, diisopropyl zinc, dioctyl zinc, diisooctyl zinc, dihexadecyl zinc, zinc diethoxide, zinc dipropoxide, zinc dibutoxide, etc.

The novel catalysts of the present invention can be prepared by reacting the amine compound with either the tin compound or the zinc compound in a suitable reaction vessel equipped with a reflux condenser or suitable column for the removal of evolved vapors and with appropriate means for controlling the temperature in the reactor. The reaction between the amine and the tin compound or zinc compound is a displacement reaction. The initial reaction mixture should contain at least an equivalent amount of amine and the amine is preferably in excess. Thus, the reaction mixture may suitably contain from about 1 to about 10 mols of amine per mol of tin compound or zinc compound. The reactivity of the reactants varies. The reaction frequently will initiate spontaneously at room temperature, but it is usually desirable to heat the reaction mixture to avoid prolonged reaction times. Temperatures within the range of about 20° to 150° C. are suitable. The reaction is preferably conducted in an inert atmosphere at reflux temperature, so long as the reflux temperature does not exceed about 150° C. During the course of the reaction low boiling products are removed from the reactor as evolved through a distillation column or a reflux condenser. The reaction is normally carried to completion by a reaction time within the range of about 1 to 5 hours.

The product of the reaction is a solid or liquid reaction product wherein the viscosity at room temperature ranges from free flowing liquids to gells.

In another aspect of the present invention, the novel catalysts are utilized to catalyze the reaction of an acrylate or methacrylate with an amine to provide an N-substituted acrylamide or methacrylamide.

This reaction is suitably conducted in a reactor in the presence of a catalytically effective amount of a catalytic compound of the present invention.

A suitable reaction procedure to be utilized is the procedure that is disclosed in copending U.S. patent application Ser. No. 469,860 referred to above.

The desired N-substituted acrylamides have the formula:

where $R^1$ is hydrogen or methyl, $R^2$ is hydrogen or lower alkyl of one to four carbon atoms and $R^3$ is alkyl, aryl, alkaryl, aralkyl or alkoxyalkyl, each of which may have one to twenty carbon atoms. The $R^3$ group may also be

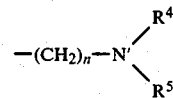

where n is an integer of from 2 to 6 and $R^4$ and $R^5$ when taken singly are lower alkyl groups containing 1 to 4 carbon atoms, or $R^4$ and $R^5$ when taken jointly are combined with the N' atom to form a heterocyclic ring group selected from the group consisting of morpholine, pyrrolidine or piperidine ring groups. These acrylamides are formed from two reactants, an acrylate ester and an amine.

The acrylate ester has the formula:

where $R^1$ is defined as above and $R^6$ is a lower alkyl of one to 4 carbon atoms.

The preferred acrylates or methacrylates are methyl acrylate, ethyl acrylate, methyl methacrylate and ethyl methacrylate since these are readily accessible industrially and the alcohol liberated upon aminolysis can easily be removed from the reaction mixture. As the number of carbon atoms in the alcohol radicals increases, the suitability of the esters decreases. For that reason, the alkyl esters having more than 4 carbon atoms in the alkyl radical are considered as less preferred. Methyl acrylate and methyl methacrylate are especially preferred.

The amines useful in this invention are primary and secondary amines containing various substituents. These amines may be represented by the formula $HNR^2R^3$ where $R^2$ and $R^3$ are defined as above. These substituents may be alkyl, aryl, alkaryl, aralkyl, dimethylaminopropyl, diethylaminopropyl, isopropylaminoethyl, t-butylaminopropyl, alkoxy and the like as a partial list not intended to limit the above definition. Examples of specific amines which would be suitable are dimethylaminoneopentanamine, 3-dimethyl-aminopropylamine, 2-dibutylamino-ethylamine, 4-(aminopropyl) morpholine, 3-diethylaminopropylamine, 2-dimethylamino-ethylamine, 1-(aminopropyl)piperidine, 4-(aminoethyl)morpholine and similar compounds. A preferred compound is 3-dimethylaminopropylamine.

The reaction should be conducted at a temperature in the range of about 50° to 150° C. Reaction pressure should be approximately atmospheric. Reduced pressures are used as required to keep the temperature within the desired range.

The catalytic reaction between the amine and the acrylate or methacrylate may be conducted batchwise or on a continuous basis. As the reaction proceeds, a lower alkyl alcohol by-product is formed. It is not essential that the alcohol be removed and in a continuous process the alcohol by-product will form a part of the reaction mixture. When batch processing is employed, it is normally desirable to utilize a reflux condenser and in this situation the by-product alcohol can be conveniently removed as it is evolved.

The N-substituted acrylamide or methacrylamide is an equimolar reaction product of the amine and the acrylate or methacrylate and the reaction can be conducted using equimolar amounts of the reactants. Preferably, however, the acrylate or methacrylate is in molar excess with respect to the amine, such as in a mol ratio of about 2 to 100 mols of acrylate or methacrylate per mol of amine.

When the reaction is being conducted batchwise, the amine may be added to the reactor in incremental portions at a rate required to maintain a desired rate of evolution of the by-product alcohol.

The invention will be further illustrated by the following examples which are not intended to limit the scope of the invention.

EXAMPLES 1–4

A blend of the following materials was prepared:
76 g methyl methacrylate* (MMA)
13.5 g 3-dimethylaminopropylamine* (DMAPA)
0.2 g N,N'-diphenyl-p-phenylene diamine
0.2 g phenothiazine
*These were predried with 4 A molecular sieves.

Then, to a culture tube containing 0.002 moles of the catalyst to be tested was added 5.0 ml of the above solution. The tubes were capped and inserted in a sand bath maintained at 100° C. After 1.25 hours, the tubes were removed and the contents analyzed by gas-liquid chromatography (glc).

The catalysts tested and the results are recorded in the following table. Note that the catalyst of this invention (Example 1) provides higher reactivity and selectivity than those of the prior art (Examples 2–4).

TABLE 1

| Experiment No. | Compound Tested (g) | G. C. Analysis (Area %) | | | | |
|---|---|---|---|---|---|---|
| | | DMAPMA[1] | Adduct[2] | DMAPA[3] | MMA[4] | CH$_3$OH |
| 1 5642-63-7 | Bis(diethylamino) dimethyl tin (0.59) | 20.9 | 0.3 | 0.5 | 60.9 | 17.4 |
| 2 5642-63-1 | Tri-n-butyltin methoxide (0.64) | 4.6 | 0.3 | 12.3 | 78.7 | 3.0 |
| 3 5642-63-3 | Dibenzyltin oxide (0.63) | 2.6 | 6.5 | 11.2 | 66.6 | 11.0 |
| 4 5642-36-2 | Dibutyltin di- methoxide (0.59) | 17.2 | 0.9 | 2.8 | 70.9 | 7.0 |

[1]N—(3-Dimethylaminopropyl)methacrylamide
[2]Michael Adduct = Methyl(3-(3-dimethylaminopropylamino)-2-methyl)propionate
[3]Dimethylaminopropylamine
[4]Methyl methacrylate

EXAMPLE 5

To a 200 ml flask equipped with a thermometer, distillation head, and condenser were charged 95 g of dry 3-dimethylaminopropylamine and 4.5 g stannous methoxide. A nitrogen atmosphere was provided, and the mixture was refluxed one hour, then 50 g DMAPA was distilled. After an additional hour of reflux the mixture was filtered in a nitrogen atmosphere to provide a yellow filtrate. The evaporation of the liquid from the sample at high vacuum (25° C.) gave ca. 2 g of a yellow-green viscous oil.

Elemental analysis showed that the sample contained 43.8% tin and 5.3% nitrogen. NMR analysis gave broad bands indicating the methoxide protons and dimethylamino protons were present in approximately equal quantities.

EXAMPLE 6

To a 100 ml flask equipped with a 12" distillation column, distillation head and condenser, magnetic stirrer, thermometer and nitrogen atmosphere were charged:
50 ml DMAPA
10 g dibutyltin dimethoxide The contents were heated to 136°–139° C. for 4.3 hours. During this time methanol and some DMAPA distilled. Evaporation of the excess DMAPA under high vacuum gave a viscous liquid.

The infrared spectrum showed an absence of N—H bonds, and showed bands at 2780 and 1060 gm$^{-1}$ indicating Sn—O—CH$_3$. The NMR spectrum showed the appropriate ratios of the following groups: butyl:methoxyl:dimethylaminopropylamine=4.4:1.8:1.0. The compound has the following structure:

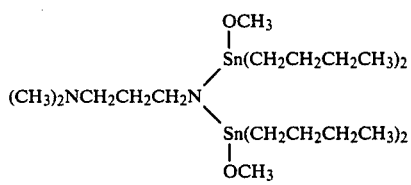

EXAMPLE 7

To a nitrogen padded 500 ml flask was charged 200 ml of anhydrous diethylether and 8.4 g of diethyl zinc. Then 17.3 ml of dry DMAPA was added dropwise with ice bath cooling at ca. 5° C.

The ether was then evaporated under vacuum, eventually increasing the temperature to 50° C. The resulting liquid gave a clear gel on standing at ambient temperature under a nitrogen atmosphere.

Proton NMR analysis (benzene-d$_6$ solvent) showed that no DMAPA (free) remained in the sample, however, dimethylamino groups in the sample were apparently strongly coordinated with zinc as evidenced by singlets at 2.2 ppm.

EXAMPLES 8–11

In a procedure identical to that used in Examples 1–4 the following catalysts were tested:

TABLE 2

| Experiment No. | | Compound Tested (g) | G. C. Analysis (Area %) | | | | |
|---|---|---|---|---|---|---|---|
| | | | DMAPMA[1] | Adduct[2] | DMAPA | MMA | $CH_3OH$ |
| 8 | 5710-3-10 | Catalyst of Ex. 5 (0.56) | 13.9 | 5.2 | 6.1 | 71.4 | 2.6 |
| 9 | 5710-21-12 | Catalyst of Ex. 6 (0.73) | 22.0 | 1.9 | 1.2 | 65.9 | 8.4 |
| 10 | 5710-28-4 | Catalyst of Ex. 7 (0.54) | 24.2 | 5.6 | 7.8 | 52.4 | 4.5 |
| 11 | 5710-28-1 | Tetrakis(diethyl-amino)tin (0.20)* | 8.3 | 1.6 | 10.6 | 72.1 | 6.5 |

[1] N—(3-Dimethylaminopropyl)methacrylamide
[2] Michael Adduct = Methyl(3-(3-dimethylaminopropylamino)-2-methyl) propionate
*Note:
Only 25% of the usual amount of catalyst was added As may be seen, all of the catalysts of Examples 8 through 11 are active and selective in the production of DMAPMA.

EXAMPLE 12

Evaluation of Bis(diethylamino)dimethyltin

To a 500 ml reaction flask, equipped with magnetic stirrer, thermometer, sampling port, addition funnel, and distillation column topped with a distilling head, were charged 215 g dry methyl methacrylate (MMA), 1.5 g each phenothiazine and N,N'-diphenyl-phenylenediamine, and 3.1 g bis(diethylamino)dimethyltin. The mixture was heated to 100° C. and 73 g of dry dimethylaminopropylamine were added dropwise over a 90 minute period. The pot temperature was allowed to increase to 119° C. while the methanol/methyl methacrylate azeotrope was removed. Analysis of the reaction mixture by gas chromatography revealed 98.4% selectivity to dimethylaminopropylmethacrylamide (DMAPMA) at 98% conversion, basis DMAPA, after 2½ hours total reaction time (from the beginning of the DMAPA addition).

The above examples are given by way of illustration only and are not intended as limitations on the scope of this invention, as defined by the appended claims.

We claim:

1. In a process for the preparation of N-substituted acrylamides or methacrylamides of the formula:

$$CH_2=\underset{R^1}{\underset{|}{C}}-\underset{O}{\overset{\|}{C}}-NR^2R^3$$

wherein $R^1$ is hydrogen or methyl, $R^2$ is hydrogen or lower alkyl of 1 to 4 carbon atoms and $R^3$ is alkyl, aryl, alkaryl, aralkyl or alkoxyalkyl containing 1 to 20 carbon atoms or

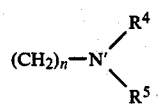

where n is an integer from 2 to 6 and $R^4$ and $R^5$ taken singly are lower alkyl groups containing 1 to 4 carbon atoms or $R^4$ and $R^5$ taken jointly are combined with the N' atom to form a heterocyclic ring group selected from the group consisting of morpholine, pyrrolidine or piperidine ring groups, which process comprises reacting an acrylate or methacrylate ester of the formula:

$$CH_2=\underset{R^1}{\underset{|}{C}}-\underset{O}{\overset{\|}{O}}-O-R^6$$

where $R^1$ is defined as above and $R^6$ is a lower alkyl of 1 to 4 carbon atoms with an amino of the formula $HNR^2R^3$ where $R^2$ and $R^3$ are defined as above;

the improvement which comprises conducting said process in the presence of a catalytically effective amount of a liquid catalyst addition compound having a nitrogen-tin or a nitrogen-zinc bond, said catalyst addition compound having been prepared my mixing at least an equimolar amount of an amine precursor compound with a tin compound or a zinc compound and reacting said mixture at a temperature within the range of about 20° to 150° C. for a period of time within the range of about 1 to 5 hours and recovering said catalyst addition compound from the products of said reaction, said amine precursor compound having the formula: $HNR^7R^8$ wherein $R^7$ is hydrogen or a $C_1$–$C^4$ alkyl group and $R^8$ is an alkyl, aryl, alkaryl, aralkyl, or alkoxyalkyl group having 1 to 20 carbon atoms, said tin compound having the formula: $R_3SnX$, $R_2SnX_2$, $RSnX_3$, $SnX_4$ or $SnX_2$ wherein R is a $C_1$–$C_{10}$ alkyl group and X is chlorine, bromine, oxygen or a $C_1$–$C_4$ alkoxide group, and said zinc compound being zinc chloride, zinc bromide, a $C_1$–$C_{18}$ zinc alkoxide or a dialkyl zinc compound wherein each alkyl group contains 1 to 4 carbon atoms.

2. In a process for the preparation of N-substituted acrylamides or methacrylamides of the formula:

$$CH_2=\underset{R^1}{\underset{|}{C}}-\overset{O}{\overset{\|}{C}}NR^2R^3$$

wherein $R^1$ is hydrogen or methyl, $R^2$ is hydrogen or lower alkyl of 1 to 4 carbon atoms and $R^3$ is alkyl, aryl, alkaryl, aralkyl or alkoxyalkyl containing 1 to 20 carbon atoms or

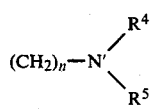

where n is an integer from 2 to 6 and $R^4$ and $R^5$ taken singly are lower alkyl groups containing 1 to 4 carbon atoms or $R^4$ and $R^5$ taken jointly are combined with the N' atom to form a heterocyclic ring group selected from the group consisting of morpholine, pyrrolidine or piperidine ring groups, which process comprises reacting an acrylate or methacrylate ester of the formula:

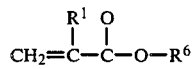

where $R^1$ is defined as above and $R^6$ is a lower alkyl of 1 to 4 carbon atoms with an amine reactant of the formula $HNR^2R^3$ where $R^2$ and $R^3$ are defined as above;

the improvement which comprises:

heating about 2 to about 100 moles of said acrylate or methacrylate eester per mole of said amine reactant at a temperature within the range of about 50° to about 150° C. in the presence of a catalytically effective amount of a liquid catalyst addition compound having a nitrogen-tin or a nitrogen-zinc bond to form said acrylamide or methacrylamide and a corresponding lower alcohol by-product, and, at the end of said reaction, recovering said acrylamide or methacrylamide from the products of said reaction, said catalyst addition compound having been prepared by mixing at least an equimolar amount of an amine precursor compound with a tin compound or a zinc compound and reacting said mixture at a temperature within the range of about 20° to 150° C. for a period of time within the range of about 1 to 5 hours and recovering said catalyst addition compound from the products of said reaction, said amine precursor compound being the same compound as said amine reactant compound, said tin compound having the formula:
$R_3SnX$, $R_2SnX_2$, $RSnX_3$, $SnX_4$ or $SnX_2$
wherein R is a $C_1$–$C_{10}$ alkyl group and X is chlorine, bromine, oxygen or a $C_1$–$C_4$ alkoxide group, and said zinc compound being zinc chloride, zinc bromide, a $C_1$–$C_{18}$ zinc alkoxide or a dialkyl zinc compound wherein each alkyl group contains 1 to 4 carbon atoms.

3. A method as in claim 2 wherein the catalyst addition compound is a zinc compound.

4. A method as in claim 3 wherein the zinc compound is diethyl zinc.

5. A method as in claim 2 wherein the catalyst addition compound is a tin compound.

6. A method as in claim 5 wherein the tin compound is a tin alkoxide.

7. A method as in claim 6 wherein the tin alkoxide is stannous methoxide.

8. A method as in claim 6 wherein the tin alkoxide is dibutyltin dimethoxide.

9. A method as in claim 5 wherein the tin compound is a compound having the formula:

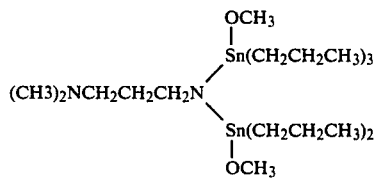

10. A method as in claim 2 wherein the catalyst addition compound is a compound made by the steps of preparing a reaction mixture of at least an equimolar amount of 3-dimethylaminopropylamine with a tin compound selected from the group consisting of stannous methoxide and dibutyltin dimethoxide and reacting said compound at a temperature within the range of about 20° to about 150° C. for a period of time within the range of about 1 to about 5 hours and recovering the liquid addition product of said amine and said tin compound from the products of said reaction for use as said catalyst addition compound 11. A method as in claim 10 wherein the tin compound is stannous methoxide.

12. A method as in claim 10 wherein the tin compound is dibutyltin methoxide.

* * * * *